(12) United States Patent
Jin et al.

(10) Patent No.: US 9,725,424 B2
(45) Date of Patent: Aug. 8, 2017

(54) 4-(5-AMINO-6-HYDROXYBENZOXAZOL-2-YL) AMMONIUM BENZOATE AND PREPARATION METHOD AND USE THEREOF

(71) Applicants: Zhejiang University of Technology, Zhejiang (CN); Yancheng Dragon Chemical Co., Ltd., Jiangsu (CN)

(72) Inventors: Ningren Jin, Zhejiang (CN); Biao He, Zhejiang (CN); Jing Jin, Zhejiang (CN)

(73) Assignees: ZHEJIANG UNIVERSITY OF TECHNOLOGY, Zhejiang (CN); YANCHENG DRAGON CHEMICAL CO., LTD., Yancheng, Jiangsu (CN)

( * ) Notice: Subject to any disclaimer, the term of this patent is extended or adjusted under 35 U.S.C. 154(b) by 281 days.

(21) Appl. No.: 14/439,952

(22) PCT Filed: Feb. 9, 2013

(86) PCT No.: PCT/CN2013/071589
§ 371 (c)(1),
(2) Date: Apr. 30, 2015

(87) PCT Pub. No.: WO2014/075403
PCT Pub. Date: May 22, 2014

(65) Prior Publication Data
US 2015/0239856 A1    Aug. 27, 2015

(30) Foreign Application Priority Data

Nov. 16, 2012 (CN) .......................... 2012 1 0465960
Nov. 28, 2012 (CN) .......................... 2012 1 0499035

(51) Int. Cl.
*C07D 263/57* (2006.01)
*D01F 6/74* (2006.01)
*C08G 73/22* (2006.01)
*D01D 5/06* (2006.01)

(52) U.S. Cl.
CPC .......... *C07D 263/57* (2013.01); *C08G 73/22* (2013.01); *D01D 5/06* (2013.01); *D01F 6/74* (2013.01); *D10B 2331/14* (2013.01)

(58) Field of Classification Search
CPC .................................................. C07D 263/57
See application file for complete search history.

(56) References Cited

FOREIGN PATENT DOCUMENTS

| CN | 101016275 A | 8/2007 |
|---|---|---|
| CN | 101209998 A | 7/2008 |

OTHER PUBLICATIONS

International Search Report in International Application No. PCT/CN2013/071589, filed Feb. 9, 2013.

*Primary Examiner* — Laura L. Stockton
(74) *Attorney, Agent, or Firm* — Saliwanchik, Lloyd & Eisenschenk

(57) ABSTRACT

Disclosed in the present invention are 4-(5-amino-6-hydroxybenzoxazol-2-yl)ammonium benzoate shown in formula (I) and the preparation method and use thereof. The preparation method comprises: fully reacting 4-(5-amino-6-hydroxybenzoxazol-2-yl)benzoic acid shown in formula (II) or 4-(5-amino-6-hydroxybenzoxazol-2-yl)carboxamide benzoate, as a raw material, with ammonia in an aqueous solvent, and directly heating the obtained reaction liquid to remove excess ammonia, so as to obtain 4-(5-amino-6-hydroxybenzoxazol-2-yl)ammonium benzoate. The mass of the 4-(5-amino-6-hydroxybenzoxazol-2-yl)ammonium benzoate (ABAA) prepared in the present invention can reach a polymer grade (where the purity is above 99.5%, the content of metal ions is below 200 ppm, and containing no DMF polymerization inhibition impurities), and the 4-(5-amino-6-hydroxybenzoxazol-2-yl)ammonium benzoate can be used as an AB type monomer for preparing PBO and modified PBO fibers, the resulting PBO having an intrinsic viscosity η of up to 38/dl/g, and the method has such features as ABAA being highly soluble in PPA, a fast polymerization speed, a short time of 2-4 h, a low temperature of 150° C., a high molecular weight of the polymer, fibers of excellent tensile property, being easy to industrialize, etc.

20 Claims, 4 Drawing Sheets

4-(5-AMINO-6-HYDROXYBENZOXAZOL-2-YL) AMMONIUM BENZOATE AND PREPARATION METHOD AND USE THEREOF

CROSS-REFERENCE TO RELATED APPLICATIONS

This application is the U.S. national stage application of International Patent Application No. PCT/CN2013/071589, filed Feb. 9, 2013, which claims priority to Chinese Application Nos. 201210465960.6, filed Nov. 16, 2012, and 201210499035.5, filed Nov. 28, 2012.

FIELD OF THE INVENTION

The present invention relates to an ammonium 4-(5-amino-6-hydroxybenzoxazol-2-yl)benzoate (abbreviated as ABAA) and its preparation and use as an AB-monomer in the preparation of PBO and modified PBO fibers.

BACKGROUND OF INVENTION

With respect to AB-type monomer of PBO, as early as 1990 there had been a research on the synthesis of 4-(5-amino-6-hydroxy-2-benzoxazol-2-yl)benzoic acid (ABA) and its use in preparing PBO resin by homo-polycondensation in a PPA solvent (Polymer preprints, 1990, 31(2), 681-682). The synthetic route is shown by Scheme (1) and Scheme (2).

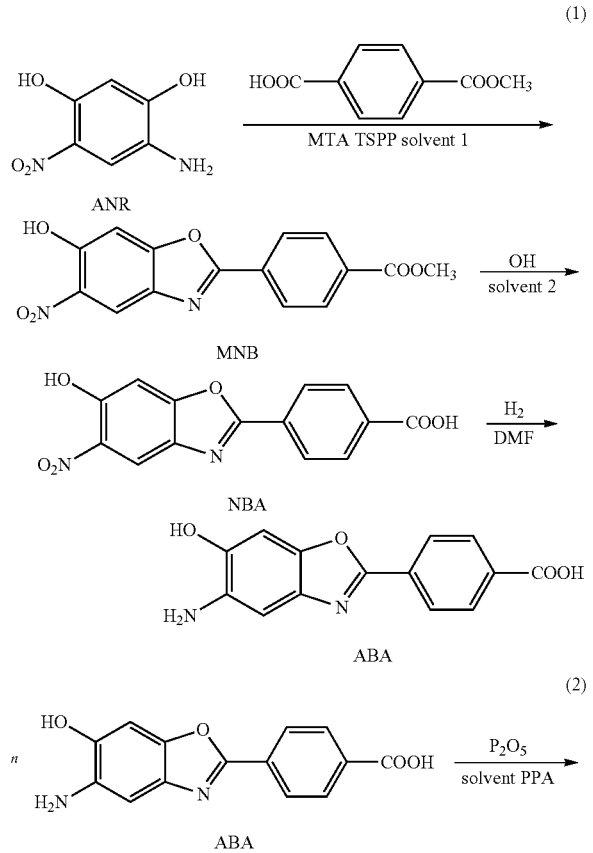

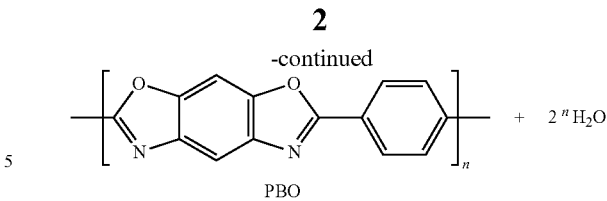

PBO

However, there was no progress subsequently until Toyo Boseki Kabushiki Kaisha developed a pilot-scale technology to synthesize PBO fibers with AB-type monomer via homo-polycondensation in 2007, which was successively reported in WO 2007032296 A1 in March 2007 and US 20080269455 A1 in October 2008. The scheme (2) completely avoided the release and interference of HCl gas, implemented the equimolar homopolymerization of polycondensation-groups, and thus the polymerization efficiency was greatly improved. However, there exist some problems in scheme (1), for example, ABA prepared by scheme (1) comprises residual DMF which is a polymerization inhibitor and is difficult to achieve polymer-grade quality, and the key starting material 4-amino-6-nitroresorcinol (ANR) for preparing ABA is easy to decompose and difficult to obtain. The purity of ABA prepared by Toyobo and recrystallized using DMF-methanol was only 99%, and the polymerization still need to be carried out by addition of antioxidant stannous chloride and under severe conditions of polymerization temperature at 220° C., total polymerization time in a twin-screw polymerization reactor of 6 h, an intrinsic viscosity [η] of 34 dl/g. The literature (Polymer preprints, 1990, 31 (2), 681-682) disclosed that the polymer with an intrinsic viscosity of up to 12.5 dl/g was obtained by feeding nitrogen under a pressure-reducing condition for 3 h instead of the addition of stannous chloride, dissolving the ABA at 90° C. for 12 h, and polymerizing the monomer at 120-200° C. for 9.5 h. Besides, there are still a lot of other problems in the process of preparing ABA by scheme (1), such as numerous steps, low yield, high price and large usage of the dehydrating agent TSPP, high cost of catalyst Pd/C, and using different organic solvents in each of the three reaction steps of the process. Therefore, the cost of preparing PBO resin by the above method is close to the selling price of PBO fibers, which is lack of practicality.

The inventor has successively designed and synthesized an AB-type PBO monomer methyl 4-(5-amino-6-hydroxybenzoxazol-2-yl)benzoate (MAB), and its key intermediate 4-amino-6-nitro resorcinol hydrochloride (ANR.HCl), and an AB-type PBO monomer ABA which is prepared from methyl 4-(5-nitro-6-hydroxybenzoxazol-2-yl)benzoate (MNB) according to Patent 1 (CN 2006 10155719.8). On the basis of all the researches above-mentioned, a new AB-type monomer named as 4-(5-amino-6-hydroxybenzoxazol-2-yl) benzoic acid carboxy-amino inner salt (ABAS) was synthesized according to Scheme (3). It has been proved that ABA prepared by hydrolyzing MNB and then reducing NBA according to Patent 1(CN 200610155719.8) and ABAS prepared by hydrolyzing MAB and then precipitating the product according to Patent 2 (CN 2006 10155718.3) are tautomers, and ABAS is a carboxy-amino inner salt of ABA.

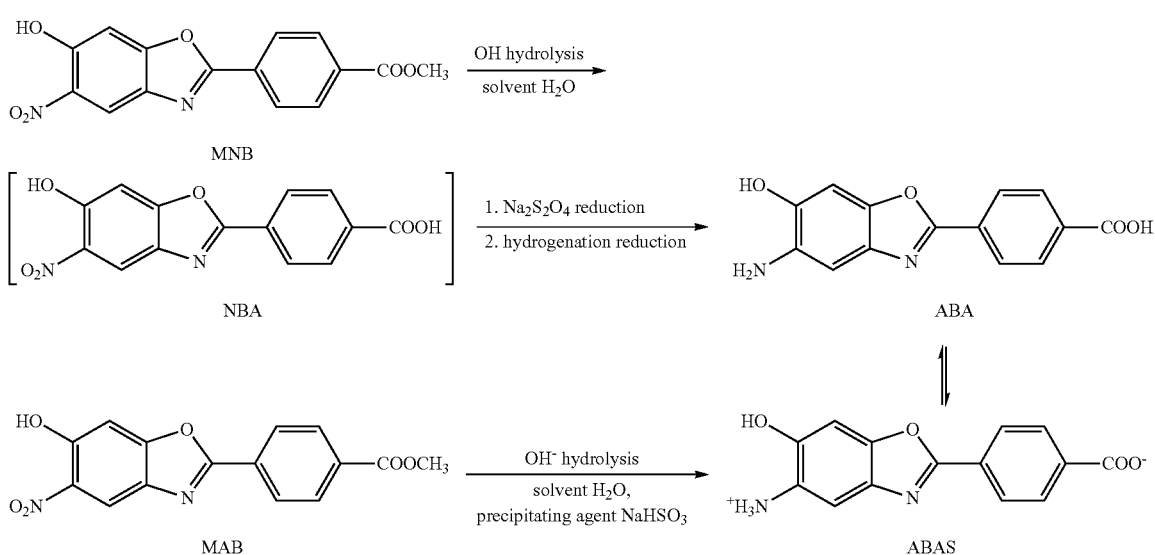

(3)

Compared with other literatures and the patents of Toyobo, the AB-type monomers prepared according to Patent 1 and Patent 2 do not contain DMF which is a polymerization inhibition impurity and have advantages of simple preparation technology and superior economy, but their application results do not improve obviously, mainly because the new AB-type monomers contain too many metal ions or couldn't reach polymer grade (specifically, the monomers prepared according to the methods disclosed in Patent 1 and Patent 2 contain a little of sulfites and metal ions with content of 5000-10000 ppm, and the processes of preparing the monomers result in pollution through waste water containing sulfites), which hinder ABA self-condensation, thereby resulting in obtaining PBO with intrinsic viscosity of only 15 dl/g, which is slightly higher than that of PBO prepared by the literature (Polymer preprints, 1990, 31 (2), 681-682). Therefore, in order to prepare PBO with ultra-high molecular weight, it is particularly important and urgent to prepare a polymer grade AB-type PBO monomer, improve the method of preparing ABA as shown in scheme (3), and develop a method with low pollution and effective removal of metal ions.

BRIEF SUMMARY

The first object of the present invention is to provide ammonium 4-(5-amino-6-hydroxy benzoxazol-2-yl)benzoate, abbreviated as ABAA, which has equimolar polycondensation groups, excellent oxidation resistance and thermal stability, and good solubility in polyphosphoric acid, and can be preserved for more than three years without any antioxidant or inert atmosphere. Therefore, it is more suitable to be an AB-type monomer to prepare PBO or modified PBO fibers compared with 4-(5-amino-6-hydroxybenzoxazol-2-yl)benzoic acid (ABA) and 4-(5-amino-6-hydroxybenzoxazol-2-yl)benzoic acid carboxy-amino inner salt (ABAS).

The second object of the present invention is to provide a method of preparing ABAA, which has advantages of easy operation, effective control of the content of metal ions in the product, and good economy and environment protection, and the product prepared by this method is found to be up to the polymerization grade, with purity of ≥99.5%, content of metal ions of 200 ppm or less, and no polymerization inhibition impurity DMF.

The third object of the present invention is to provide use of ABAA in preparing PBO and modified PBO fibers, which has advantages in simplifying procedure, speeding up the rate of polymerization, lowing polymerization temperature and obtaining PBO and modified PBO with high molecular weight and excellent tensile performance.

The technical solutions of the present invention are specifically described below.

The present invention provides a new compound of formula (I), which is called ammonium 4-(5-amino-6-hydroxybenzoxazol-2-yl)benzoate (ABAA),

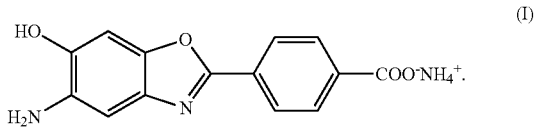

(I)

The present invention also provides a method of preparing ABAA, which includes the following step:

1) Using 4-(5-amino-6-hydroxybenzoxazol-2-yl)benzoic acid of formula (II) (ABA) or 4-(5-amino-6-hydroxybenzoxazol-2-yl)benzoic acid carboxy-amino inner salt of formula (III) (ABAS,) as a raw material, reacting the raw material with ammonia in water, after the reaction is completed, removing excess ammonia from the reaction solution by heating and keeping water content in the reaction solution constant during the process of removing ammonia, then cooling the reaction solution, subjecting it to filtration, washing and drying the solids to obtain ammonium 4-(5-amino-6-hydroxybenzoxazol-2-yl) benzoate (ABAA);

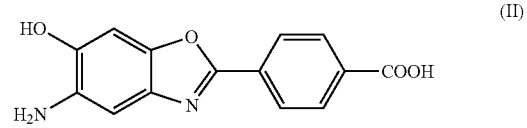

(II)

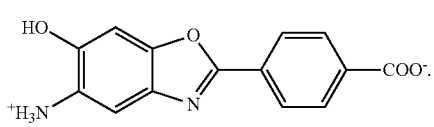

(III)

In the present invention, the raw material ABA or ABAS used in step 1) can be prepared with different methods according to the known literature, and differs in purity and content of metal ions therein. For example, ABA or ABAS prepared according to Patent 1 (CN 200610155719.8) contains high content of metal ions, which would affect the quality of the product ABAA. In step 1) of the present invention, no extra metal ions are introduced by any substances, thus, for the raw material (ABA or ABAS) with different content of metal ions, the content of metal ions in ABAA can be estimated by the mass ratio of deionized water added to the reaction system to the raw material, and the quality of ABAA can be effectively controlled. In step 1), the mentioned ammonia is added in the form of refined ammonia water (e.g. refined 25% ammonia water), and the water added to the reaction system is deionized water. The solubility of the raw material in the system depends on dosages of ammonia and water. In this invention, the molar ratio of ammonia to the raw material (ABA or ABAS) is preferably between 8:1 and 30:1, more preferably between 18:1 and 28:1. The water (including deionized water and the water in ammonia water) is 16~70 times, preferably 24~56 times, more preferably 24~28 times the weight of the raw material (ABA or ABAS).

Preferably, in step 1), the reaction of the raw material (ABA or ABAS) with ammonia is carried out at 40~80° C., with stirring until dissolved.

Preferably, in step 1), removing excess ammonia by heating is carried out at a temperature not higher than 80° C. until the pH of the reaction system reaches 7.0~7.5. More preferably, removing excess ammonia by heating is carried out at 60~80° C. until the pH of the reaction system reaches 7. During the process of ammonia removal, yellow crystals continuously precipitate out, and the content of water in the reaction system is kept constant (e.g. by using reflux condenser) to avoid the adverse effect of concentration of the reaction system on the quality of the product. The removed ammonia can be recovered as ammonia water.

Further, if the raw material contains high content of impurities (e.g. metal ions), step 1) includes a step of impurity removal as follows: adding activated carbon into the reaction solution to absorb the impurities, then subjecting the reaction system to filtration to remove waste carbon, and directly heating the filtrate to remove excess ammonia. Preferably, activated carbon is added in the form of powder, and is 0.05~0.13 times, more preferably 0.1 times the weight of the raw material (ABA or ABAS). Preferably, absorbing the impurities with activated carbon is carried out at 60~90° C.

Further, in order to avoid oxidation of the raw material and the product ABAA in the high-temperature alkaline aqueous solution, step 1) includes an antioxidation step as follows: adding ammonium sulfite to the reaction solution as an antioxidant (if the step of impurity removal with activated carbon has been carried out, ammonium sulfite is added to the filtrate obtained in the step of impurity removal), and then directly heating the mixture to remove excess ammonia. Preferably, ammonium sulfite is 0.14~0.50 times, more preferably 0.15~0.25 times the weight of the raw material (ABA or ABAS).

Further, if ABAA prepared by step 1) still can not be up to the polymerization grade, the method can also include a refining step 2) as follows:

2) Dissolving ABAA with ammonia water to obtain an ABAA solution, heating the solution to remove excess ammonia, keeping the content of water in the system constant during the process of ammonia removal, then cooling the reaction solution, subjecting it to filtration, washing and drying the solids to obtain refined ABAA.

In step 2), ammonia water is added in the form of diluting refined ammonia water (e.g. 25% refined ammonia water) with deionized water. Preferably, the molar ratio of ammonia to ABAA is between 8:1 and 30:1, more preferably between 18:1 and 28:1. The water added to the system (including deionized water and the water contained in ammonia water) is 16~70 times, preferably 2456 times, more preferably 4856 times the weight of ABAA.

Preferably, in step 2), dissolving ABAA with ammonia water is carried out at 40~80° C., with stirring until dissolved to obtain an ABAA solution.

Preferably, the operating conditions of the process of removing excess ammonia by heating in step 2) are identical with those in step 1).

Further, in order to effectively remove metal ions, step 2) also includes a step of impurity removal with activated carbon as follows: adding activated carbon into the ABAA solution to absorb impurities, then subjecting the mixture to filtration to remove waste carbon, and directly heating the filtrate to remove excess ammonia. The activated carbon is 0.05~0.13 times, preferably 0.1 times the weight of ABAA. The operating conditions of the process of absorbing impurities with activated carbon in step 2) are identical with those in step 1).

Further, in order to avoid oxidation of ABAA in the high-temperature alkaline aqueous solution, step 2) can also include an antioxidation step as follows: adding ammonium sulfite to the ABAA solution as an antioxidant (if the step of impurity removal with activated carbon has been carried out, ammonium sulfite is added to the filtrate obtained in the step of impurity removal), and then directly heating the mixture to remove excess ammonia. Ammonium sulfite is 0.14~0.50 times, preferably 0.15~0.25 times the weight of ABAA.

In the present invention, times of refining can be determined by the person skilled in the art according to actual situation to make ABAA ultimately obtained to reach the polymerization grade.

Further, in order to obtain 4-(5-amino-6-hydroxybenzoxazol-2-yl)benzoic acid (ABA) which contains low content of metal ions and no polymerization inhibition impurity DMF, and would not produce harmful gas during the process of preparing PBO as the raw material, an one-pot method of preparing ABA is provided by the present invention, which is carried out according to scheme A or scheme B:

scheme A: subject methyl 4-(5-nitro-6-hydroxybenzoxazol-2-yl)benzoate (MNB) of formula (IV) to hydrolysis of ester group, then subject the intermediate of formula (V) to reduction of nitro group, thereby obtain ABA;

scheme B: subject methyl 4-(5-nitro-6-hydroxybenzoxazol-2-yl)benzoate (MNB) of formula (IV) to reduction of nitro group, then subject the intermediate of formula (VI) to hydrolysis of ester group, thereby obtain ABA;

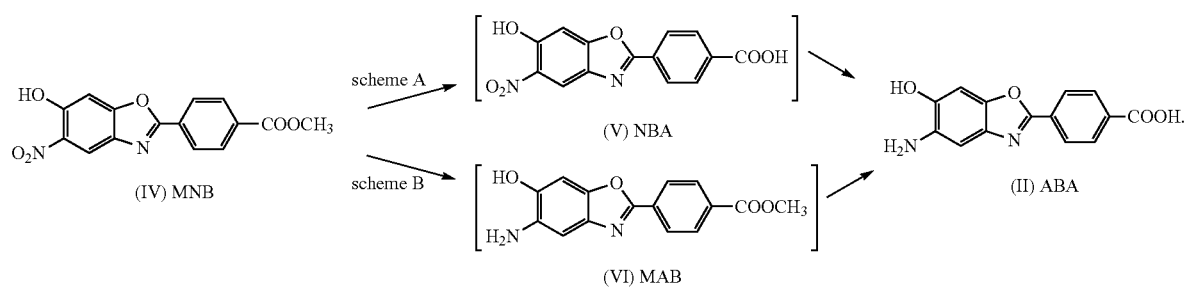

(5)

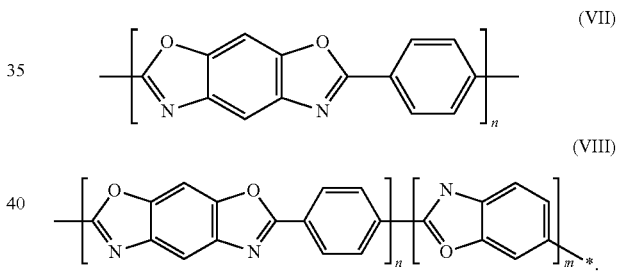

In scheme A and scheme B, alcohol-water is used as a solvent in both the reduction of nitro group and the hydrolysis of ester group, hydrazine hydrate is used as a reductant and $Fe^{2+}/C$ or $Fe^{3+}/C$ as a catalyst in the reduction of nitro group, and caustic alkali is used as a hydrolytic agent in the hydrolysis of ester group.

Preferably, the alcohol can be methanol, ethanol, isopropanol, etc., and methanol is preferred. The catalyst is composed of activated carbon and a water-soluble ferric or ferrous salt, in which $Fe^{2+}$ represents a ferrous salt such as ferrous chloride, ferrous sulfate, etc.; $Fe^{3+}$ represents a ferric salt such as ferric chloride, ferric sulfate, etc.

Preferably, both of the hydrolysis of ester group and the reduction of nitro group are carried out at reflux temperature, reaction time of the hydrolysis of ester group is between 0.5 h and 3 h, and reaction time of the reduction of nitro group is between 1.25 h and 4.5 h. The product is obtained by simple aftertreatment after the reduction of nitro group.

Preferably, the aftertreatment above-mentioned adopts the following steps: after the reaction, removing waste carbon by filtration while hot, adding hydrochloric acid into the filtrate to precipitate solids, subjecting the mixture to filtration, washing the solids with water and vacuum drying them to obtain the product ABA.

Scheme A is specifically carried out as follows:
add methyl 4-(5-nitro-6-hydroxybenzoxazole-2-yl)benzoate (MNB) of formula (IV) as a starting material, alcohol-water as a solvent and KOH as a hydrolytic agent, carry out hydrolysis of ester group at reflux temperature for 0.5~2.5 h to obtain 4-(5-nitro-6-hydroxybenzoxazol-2-yl)benzoic acid of formula (V); then without any separation add $Fe^{2+}/C$ or $Fe^{3+}/C$ as a catalyst and hydrazine hydrate as a reductant to the reaction system, carry out reduction of nitro group at reflux temperature, after reacting for 1.25~4.5 h, subject the reaction solution to aftertreatment to obtain ABA; in which the weight ratio of water to MNB is between 1.9:1 and 3.8:1, the weight ratio of alcohol to MNB is between 13:1 and 26:1, the molar ratio of KOH to MNB is between 2.50:1 and 2.82:1, the molar ratio of hydrazine hydrate to MNB is between 4:1 and 4.5:1, the weight ratio of the water-soluble ferrous or ferric salt to MNB is between 0.08:1 and 0.12:1, and the weight ratio of activated carbon to MNB is between 0.17:1 and 0.21:1.

Scheme B is specifically carried out as follows:
add methyl 4-(5-nitro-6-hydroxybenzoxazole-2-yl)benzoate (MNB) of formula (IV) as a starting material, hydrazine hydrate as reductant, an alcohol as a solvent and $Fe^{3+}/C$ or $Fe^{2+}/C$ as a catalyst, carry out reduction of nitro group at reflux temperature for 2~4 h to obtain methyl 4-(5-amino-6-hydroxybenzoxazole-2-yl)benzoate of formula (VI), without separation addNaOH and water to the reaction system, carry out hydrolysis of ester group at reflux temperature, after reacting for 1~3 h, subject the reaction system to aftertreatment to obtain ABA; in which, the alcohol is 11.2~20.5 times the weight of MNB, the molar ratio of hydrazine hydrate to MNB is between 2.47:1 and 3.35:1, the weight ratio of the water-soluble ferric or ferrous salt to MNB is between 0.12:1 and 0.15:1, the weight ratio of activated carbon to MNB is between 0.18:1 and 0.21:1, the molar ratio of NaOH to MNB is between 3.09:1 to 4.19:1, and the water is 0.2~0.8 times the weight of MNB.

The present invention further provides the use of ABAA in preparing PBO of formula (VII) by homo-polycondensation or modified PBO of formula (VIII) by co-polycondensation, Further, the use comprises:
using polyphosphoric acid(PPA) as a solvent, phosphorus pentoxide as a dehydrating agent, and nitrogen as protective atmosphere, subjecting ABAA to homo-polycondensation to obtain a liquid crystalline solution of PBO or subjecting ABAA and 4-amino-3-hydroxybenzoic acid to co-polycondensation to obtain a liquid crystalline solution of modified PBO, and then preparing PBO of formula (VII) or modified PBO of formula (VIII) fibers by dry-jet wet spinning of the liquid crystalline solution. Preferably, in the preparation of modified PBO fibers, the weight ratio of ABAA to 4-amino-3-hydroxybenzoic acid is between 60% to 40% and between 80% to 20%.

More further, the use in preparing PBO fibers includes the following steps:
A) adding monomer ABAA into polyphosphoric acid with a concentration of $P_2O_5$ more than 84 wt. % until the mass concentration of ABAA is 12-15%, heating the mixture gradually to 100-160° C. and reacting for 2~5 h in nitrogen to obtain a liquid crystal spinning solution of PBO;
B) directly and continuously subjecting the liquid crystal spinning solution of PBO to wire drawing and then aftertreatment to obtain PBO fibers of formula (VII).

More further, the use in preparing modified PBO fibers includes the following steps:

a) adding monomers composed of ABAA and 4-amino-3-hydroxybenzoic acid with a mass ratio of ABAA to 4-amino-3-hydroxybenzoic acid between 60% to 40% and 80% to 20% into polyphosphoric acid with a concentration of $P_2O_5$ more than 84% (wt) until the total mass concentration of the monomers is between 12% and 15%, heating the mixture gradually to 80~170° C. and reacting for 2-5 h in nitrogen to obtain a liquid crystal spinning solution of modified PBO;

b) directly and continuously subjecting the liquid crystal spinning solution of modified PBO to wire drawing and then aftertreatment to obtain modified PBO fibers of formula (VIII).

In the above-mentioned use in preparing PBO and modified PBO fibers, polymerization grade ammonium 4-(5-amino-6-hydroxybenzoxazol-2-yl)benzoate with purity of more than 99.5%, content of metal ions of 200 ppm or less and no polymerization inhibition impurity DMF, is preferred.

The aftertreatment in step B) and b) includes conventional fiber solidification, washing and drying.

The PBO resin produced by the present invention has an intrinsic viscosity ranging from 18 dl/g to 39 dl/g, PBO fibers have a fiber diameter ranging from 20 μm to 120 μm and fineness of 1.1 tex, and the PBO filament fiber has tensile strength of the filament ranging from 3.8 GPa to 4.2 GPa.

The modified PBO resin produced by the present invention has an intrinsic viscosity ranging from 14 dl/g to 25 dl/g, and the modified PBO filament fiber has tensile strength between 2.8 GPa and 3.6 GPa.

Compared to existing technologies, the beneficial effects of the present invention are introduced as follows:

1) ABAA is a new substance which has good application value and special characteristics described as follows:

ABAA has a stable ionic bond, does not contain tautomeric ABA or ABAS which has oxidization, and thus has excellent oxidation resistance;

ABAA contains three equimolar groups for polycondensation, has initial decomposition temperature up to 260° C. and excellent thermal stability, and can be stored for at least 3 years while the quality of ABAA stays the same under environmental conditions without any antioxidant or inert gas to protect;

besides, it has favorable solubility in PPA;

Therefore, it is an inevitable trend that ABAA will replace ABA (AB-type monomer, grayish yellow, shelf life of 10 months) and DAR.2HCl (AA-type monomer, white crystal, shelf life of 3 months) to prepare PBO fibers or modified PBO fibers.

2) ABAA prepared by the present invention can reach the polymerization grade (with purity of ≥99.5%, content of metal ion of 200 ppm or less, and no polymerization inhibition impurity DMF), and has obvious advantages in preparing PBO resin and fibers. When ABAA is dissolved in PPA, ammonium polyphosphate is produced by ammonia exchange between ABAA and PPA, and then ammonium polyphosphate partially decomposes at high temperature to release ammonia gas and produce highly active ABA, in which ammonia gas can replace stannous chloride in the polymerization system as an antioxidant because of its reducibility, and the produced ABA, due to its high activity and high solubility in PPA, can greatly accelerate the rate of polymerization, raise production capacity and produce PBO with higher molecular weight. For example, for the preparation of PBO in a 40 mL glass polymerization reactor, compared with homo-poly condensation of ABA and mixed polycondensation of DAR-TPA, homo-polycondensation of ABAA has advantages of lower polymerization temperature at 100~160° C. and better spinnability. PBO with an intrinsic viscosity ranging from 24 dl/g to 39.5 dl/g can be prepared from ABAA within a short time, and the PBO filament fiber is drawn manually and continuously and has tensile strength of up to 3.8 GPa and tensile modulus of 250 GPa. Additionally, due to low content of metal ion in ABAA and no addition of antioxidant $Sn^{2+}$ in the process, recovering and recycling of PPA can be realized with great advantages in industrialization, environmental protection and economic aspect.

3) The method of preparing ABAA has advantages as follows: ① The product prepared by the routine reaction of benzoic acid and ammonia can't be precipitated from the reaction solution until the reaction solution is concentrated to supersaturation, but in turn, the quality of the product benzoic acid ammonium salt would decreased when the solution is concentrated to supersaturation. In order to solve this problem, water content in the system is kept constant in the process of ammonia removal in the present invention, to avoid the reduction in quality of the product. ② no extra metal ions are introduced to the reaction system in step 1) and refining step 2), so for the raw material (ABA, ABAS or ABAA crude) with different metal content, the content of metal ions in ABAA can be estimated by the mass ratio (or multiples) of deionized water added to the system to the raw material, and whether refining is required and times of refining required can be determined, thus the quality of ABAA is effectively controlled. ③ The impurities can be effectively removed by the adsorption and decolorization with activated carbon. ④ The oxidation of the raw material and product ABAA in the high-temperature alkaline aqueous solution can be effectively prevented by the addition of antioxidant in the present invention. ⑤ In the present invention, ammonia removed by the ammonia removal step can be recovered after absorbed by the water, which can effectively avoid inorganic ammonium salts pollution resulting from commonly used acid-alkali refining (said acid-alkali refining comprises dissolving the crude in ammonia water, and then precipitating the product with inorganic acid). In a word, the present method of preparing ABAA has advantages of easy operation, effective control of the content of metal ions, and good economy aspect and environmental protection, and the product ABAA prepared with this method can be up to the polymerization grade, with purity of ≥99.5%, content of metal ions of 200 ppm or less, and no polymerization inhibition impurity DMF.

4) The synthetic method of ABA has advantages as follows:

(1) ABA is synthesized using alcohol-water as a solvent with one-pot method of hydrolysis and hydrazine hydrate reduction from MNB. It avoids complex procedures, such as multi-step synthesis of MNB-NBA-ABA and catalytic hydrogenation in literature, and has advantages of simple and safe operation, routine equipment, economic saving, and less pollution resulting from organic solvents. ABA prepared by present invention has advantages of high purity, no polymerization inhibition impurity DMF and good effect of polycondensation. Compared to the method of preparing ABA disclosed in the previous Patent CN 200610155719.8 which comprises hydrolyzing the raw material MNB and then reducing the hydrolysis product with sodium hyposulfate, the method in the present invention has more easily controlled and stable process, and higher yield, and obtains ABA with lower content of sodium ion due to replacement of sodium hyposulfate with hydrazine hydrate as reductant, thereby resulting in higher efficiency of the reaction of preparing ABAA. Compared to the method of preparing ABA which comprises reducing the raw material MNB according to Patent CN 200410093359.4 and then hydrolyzing the reduction product according to Patent CN 200610155718.3, the method in the present invention is simpler and has higher yield.

(2) In the one-pot method of preparing ABA from MNB, alcohol-water is used as a solvent for both the hydrolysis and reduction reaction, and it is convenient to recover and recycle the solvent. The water content of the recovered solvent is 30%, the person skilled in the art do not need to involve rectification to separate alcohol from water and only needs to accurately measure the alcohol content of the recovered solvent to determine how much alcohol or water is required to be supplemented to the recovered solvent, and then the water or alcohol can directly be added to the recovered solvent to achieve its recycle-using. The recovery rate of the solvent is up to 95%, which totally reaches the goal of clean production.

DETAILED DISCLOSURE

The technical solutions of present invention are further introduced by the examples as follows:

EXAMPLE 1

Figure 1:
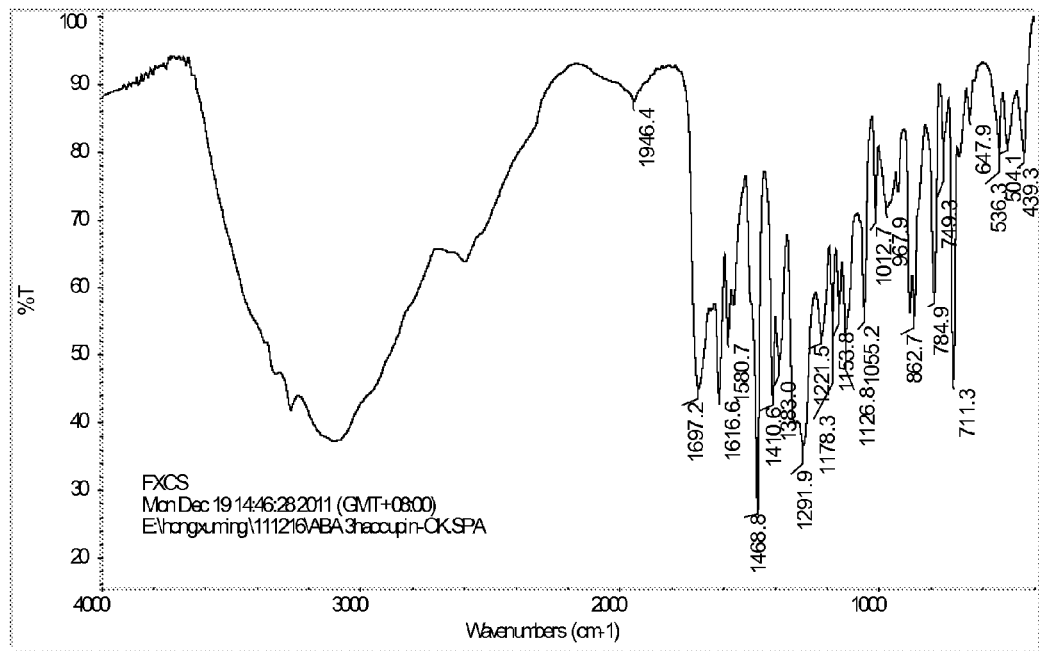
FIG. 1 is the infrared spectrum of the product ABA.
Figure 2:
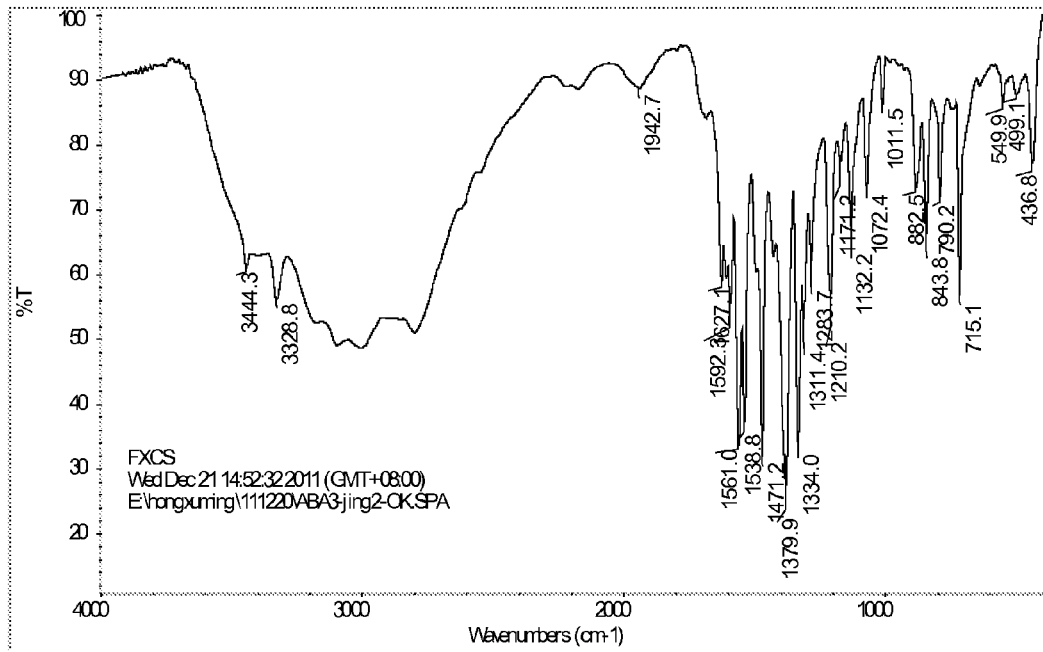
FIG. 2 is the infrared spectrum of the product ABAA.

Using ABA as the Raw Material to Prepare ABAA (1) 13.5 g (0.05 mol) of crude ABA (with purity of 98.82%, $K^+$:5489 ppm, $Na^+$:155 ppm, Fe:75 ppm, IR: FIG. 1) and 326 mL of deionized water were added into a reaction vessel. The mixture was stirred and heated to 60° C., and 50 g of 25% ammonia water (0.73 mol) was dropwise added within 5 min. After ABA dissolved, 1.5 g of activated carbon was added and the reaction mixture was heated to 80° C. After adsorbing impurities for 10 min, the reaction mixture was filtered at 65~70° C., then, 4.5 g of ammonium sulfite was added into the filtrate, and ammonia was removed from the filtrate at 60~80° C. for 1 h in vacuum until the pH of filtrate was 7.0. The reaction solution was cooled to room temperature and filtered again, the filter cake was mixed with 150 mL of deionized water, the mixture was filtered and the resulting filter cake was vacuum dried at 60° C. to get 10.8 g (0.0376 mol) of ABAA, which was a yellow crystal with purity of 99.41%, total content of metal ions of 176 ppm ($K^+$: 161 ppm, $Na^+$: 15 ppm, Fe: 0 ppm), and a yield of 75.26%. Its IR spectrum was showed in FIG. 2. IR (KBr, cm$^{-1}$) 3328.8(m), 1627.1(m), 1592.3(s), 1561.0(s), 1538.8 (s), 1379.9(s), 1334.0(s), 1311.4(s), 1210.2(s), 1132.2(s), 1072.4(s), 882.5 (s), 843.8(s), 790.2(s), 715.1(s), 436.8(s). Theoretical calculation of $C_{14}H_{13}N_3O_4$ (ABAA) element analysis: C, 58.53, H, 4.56, N, 14.63, O, 22.28. Measured: C, 58.55, H, 4.43, N, 13.44. So the product was determined qualitatively as ammonium 4-(5-amino-6-hydroxybenzoxazole-2-yl)benzoate (ABAA).

(2) 13.5 g of ABA (prepared with NBA hydrogenation method of the literature, with purity of 94.21%, $K^+$:264 ppm, $Na^+$:347 ppm, Fe:132 ppm, IR similar to FIG. 1) was added, amounts of other materials used and operating conditions were the same as step (1). After vacuum dried at 60° C., 7.6 g (0.0265 mol) of ABAA, which was a khaki crystal with purity of 97.51%, total content of metal ions of 132 ppm ($K^+$: 16 ppm, $Na^+$: 67 ppm, Fe: 49 ppm), and a yield of 52.96%, was obtained. ABAS-IR is the same as FIG. 2.

EXAMPLE 2

Using Crude ABA as the Raw Material to Prepare ABAA 20.0 g (0.074 mol) of crude ABA (with purity of 98.22%, content of inorganic salts of 10%, $K^+$: 362 ppm, $Na^+$: 50773 ppm, Fe: 239 ppm, IR similar to FIG. 1, prepared by NBA-sodium dithionite reduction in Patent CN 200610155719.8) and 400 mL of deionized water were added into a reaction vessel. The mixture was stirred and heated to 75° C., and 120 g of 25% ammonia water (1.76 mol) was added dropwise within 5 min. After the crude ABA dissolved, 2.0 g of activated carbon was added and the mixture was heated to 80° C. After adsorbing purities for 10 min, the mixture was filtered at 65~70° C., then, 5.0 g of ammonium sulfite was added into the filtrate, ammonia was removed at 55~70° C. for 1 h and 20 min in vacuum until the pH of filtrate was 7.0, then the filtrate was cooled to room temperature and filtered again. The filter cake was mixed with 200 mL of deionized water, the mixture was filtered and the resulting filter cake was vacuum dried at 60° C. to obtain 15.8 g (0.055 mol) of ABAA, which was a yellow crystal with purity of 99.27% ($K^+$: 34 ppm, $Na^+$: 3692 ppm, Fe: 22 ppm), and a yield of 74.32%. ABAS-IR spectrum was the same as FIG. 2, IR (KBr, cm$^{-1}$) 3328.2(s), 1627.5(s), 1559.9(s), 1538.1(s), 1471.2(s), 1379.4(s), 1334.0(s), 1311.1 (s), 1209.5(s), 1132.5(s), 1072.8(s), 883.9(s), 843.8 (s), 789.8(s),714.6(s).

EXAMPLE 3

Figure 3:
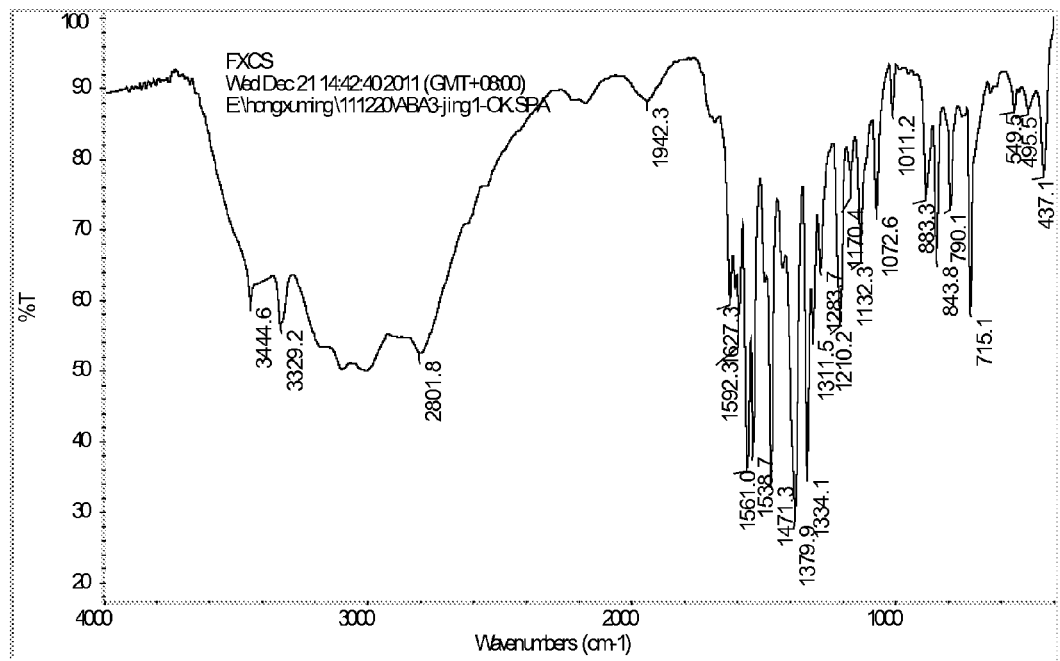
FIG. 3 is the infrared spectrum of the refined ABAA.

Using ABAA as the Raw Material to Prepare ABAA 10.0 g of ABAA prepared by example 2 (with purity of 99.27%, $K^+$: 34 ppm, $Na^+$: 3692 ppm, Fe: 22 ppm) and 500 mL of deionized water were added into a reaction vessel. The mixture was stirred and heated to 60° C., and 70 g of 25% ammonia water (1.03 mol) was dropwise added within 5 min. After ABAA dissolved, 1.0 g of activated carbon was added and the mixture was heated to 80° C. After adsorbing impurities for 10 min, the mixture was filtered at 65~70° C., then, 2.3 g of ammonium sulfite was added into the filtrate. Ammonia was removed at 60~80° C. for 1 h in vacuum until the pH of filtrate was 7.5, then the filtrate was cooled to room temperature and filtered again. The filter cake was mixed with 150 mL of deionized water, the mixture was filtered and the resulting filter cake was vacuum dried at 60° C. to obtain 8.1 g of refined ABAA, which was a yellow crystal with purity of 99.53%, total content of metal ions of 176 ppm (K 0.0 ppm, Na 176 ppm, Fe 0.0 ppm), and a yield of 81.0%. The quality of refined ABAA reached the polymerization grade. ABAA-IR spectrum was showed in FIG. 3. IR (KBr, $cm^{-1}$) 3329.2(s), 1627.3(s), 1592.3(s), 1561.0(s), 1538.7(s), 1379.9(s), 1334.1(s), 1311.5 (s), 1210.2(s), 1132.3(s), 1072.6(s), 883.3(s), 843.8(s), 790.1(s), 715.1(s), 437.1(s).

EXAMPLES 4~11

Figure 4:
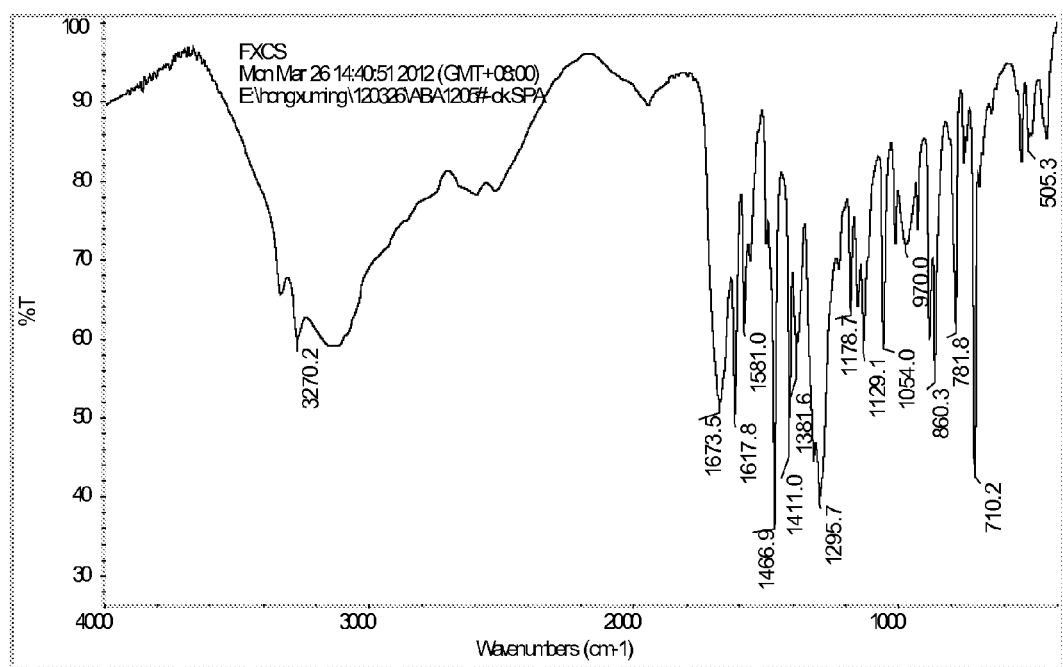
FIG. 4 is the infrared spectrum of the refined ABAS recrystallized with DMF-methanol.

ABAA and polymerization grade ABAA were prepared under different conditions such as different weight ratio of $H_2O$ to the raw material, molecular ratio of $NH_3$ to the raw material, weight ratio of ammonium sulfite to the raw material and weight ratio of activated carbon to the raw material, other operating conditions were the same as those in example 1, 2, 3. The results were showed in Table 1:

filtered, and then the resulting filter cake was vacuum dried at 60° C. to obtain 2.6 g of refined product, which was a light-gray crystal with purity of 98.04%, and a yield of 52%. The IR spectrum was showed in FIG. 4, IR (KBr, $cm^{-1}$): 3270.2(m), 1673.5(s), 1617.8(s), 1581.0(s), 1466.9(s), 1411.0(s), 1381.6(s), 1295.7(s), 1178.7(s), 1129.1(s), 1054.0 (s), 970.0(s), 860.3(s), 781.8(s), 710.2(s), 505.3(s). Theoretical calculation of $C_{14}H_{10}N_2O_4$ (ABA) element analysis: C, 62.22; H, 3.73; N, 10.37; O, 23.68. Measured: C, 61.86; H, 3.49; N, 10.85. So the product was determined qualitatively as 4-(5-amino-6-hydroxybenzoxazol-2-yl)benzoic acid (ABA) and the metal content was showed in Table 2.

TABLE 1

| Exp. | mass of Raw material (RM $^a$) (g) | $H_2O$/ RM (wr) $^b$ | $NH_3$/ RM (mr) $^b$ | $(NH_4)_2SO_3$/ RM (wr) | C/RM (wr) | Purity of ABAA (%) | content of Metal ion in ABAA/ppm $K^+$ | $Na^+$ | Fe | total metal ions/ ppm | Yield of ABAA/ % | Ref. Exp. |
|---|---|---|---|---|---|---|---|---|---|---|---|---|
| 4 | ABA 40.5 | 24.4 | 66.5 | 0.15 | 0.10 | 99.35 | 475 | 98 | 13 | 586 | 73.38 | 1(1) |
| 5 | ABA 13.5 | 21.4 | 28.8 | 0 | 0.10 | 99.15 | 511 | 159 | 18 | 688 | 65.50 | 1(1) |
| 6 | ABA 13.5 | 75.7 | 8.8 | 0.17 | 0.11 | 99.45 | 167 | 48 | 5 | 220 | 71.01 | 1(1) |
| 7 | ABA 13.5 | 69.4 | 14.7 | 0.17 | 0.07 | 99.52 | 239 | 101 | 0 | 340 | 71.78 | 1(1) |
| 8 | crude ABA 20 | 13.3 | 17.3 | 0.14 | 0.10 | 98.73 | 125 | 366 | 2 | 493 | 71.49 | 2 |
| 9 | ABAA 10 | 55.3 | 27.8 | 0.23 | 0.10 | 99.42 | 198 | 0 | 0 | 198 | 82.00 | 3 |
| 10 | ABAS 20 | 31.5 | 7.9 | 0.20 | 0 | 98.68 | 247 | 1017 | 15 | 1279 | 74.70 | 1(1) |
|  | ABAA 15.8 | 16.1 | 11.9 | 0.15 | 0 | 99.00 | 32 | 386 | 0 | 418 | 83.50 | 3 |
| 11 | ABA* 4.0 | 21.3 | 59.5 | 0.50 | 0.13 | 98.21 | 37 | 49 | 26 | 112 | 54.93 | 1(2) |

$^a$ RM: Raw material
$^b$ wr: weight ratio, mr: molecular ratio

The raw material ABA was the same as that of example 1(1), and had purity of 98.82%, content of $K^+$ of 5489 ppm, $Na^+$ of 155 ppm, Fe of 75 ppm.

The raw material crude ABA was prepared according to Patent CN 200610155719.8, and had purity of 98.02%, content of $K^+$:662 ppm, $Na^+$: 13773 ppm, Fe: 39 ppm.

The raw material ABAS was prepared according to Patent 2 CN 200610155718.3, and had purity of 98.57%, content of $K^+$: 573 ppm, $Na^+$: 28390 ppm, Fe:109 ppm.

The raw material ABA* was the same as that of example 1(2), and had purity of 94.21%, content of $K^+$:264 ppm, $Na^+$:347 ppm, Fe: 132 ppm.

COMPARATIVE EXAMPLE 1

DMF-$CH_3OH$ Recrystallization of ABAS 5.0 g of ABAS (with purity of 98.57%, $K^+$:573 ppm, $Na^+$:28390 ppm, Fe:109 ppm. prepared according to Patent 2 CN 200610155718.3) was added into a mixed solvent of 150 mL of DMF and 50 mL of $CH_3OH$. The mixture was stirred and heated to 90° C. for 30 min until ABAS was dissolved. 0.5 g of activated carbon was added to adsorb impurities at 95° C. After 15 min, the reaction mixture was filtered, and 300 mL of methanol was added into the filtrate to precipitate crude product. The crude product was sequentially mixed with 50 mL and 100 mL of methanol and

COMPARATIVE EXAMPLE 2~3

DMF-$CH_3OH$ Recrystallization of ABA

COMPARATIVE EXAMPLE 2

5.0 g of ABA (the same as example 1(1), with purity of 98.82%, $K^+$: 5489 ppm, $Na^+$: 155 ppm, Fe: 75 ppm) was added into a mixed solvent of 150 mL of DMF and 50 mL of $CH_3OH$. The mixture was stirred and heated to 90° C. for 30 min until ABA was dissolved. 0.5 g of activated carbon was added to adsorb impurities at 95° C. After 15 min, the reaction mixture was filtered, and 300 mL of methanol was added into the filtrate to precipitate crude product. The crude product was sequentially mixed with 50 mL and 100 mL of methanol and filtered, and then the resulting filter cake was vacuum dried at 60° C. to obtain 3.95 g of refined product ABA, which was a deep beige crystal, with purity of 98.01%, and a yield of 79%. ABA-IR spectrum of the product was the same as FIG. 4, IR (KBr, $cm^{-1}$) 3271.1(m), 1682.7(s),1617.9(s), 1581.2(s), 1467.4(s), 1410.8(s), 1381.0 (s), 1293.4(s), 1178.6(s), 1128.6(s), 1054.4(s), 971.9(s), 860.6(s), 781.9(s), 710.4(s), 505.2(s). So the product was determined qualitatively as ABA and the metal content was showed in Table 2.

COMPARATIVE EXAMPLE 3

5.0 g of Crude ABA (with purity of 94.21%, K: 264 ppm, Na: 347 ppm, Fe: 132 ppm. prepared by hydrolyzing MNB to obtain NBA according to scheme (3) in Patent 1(CN 200610155719.8), and then catalytic hydrogenating NBA in DMF according to scheme (1)) was added, and the feed ratios and operating conditions were the same as those of Comparative Example 1. After vacuum dried at 60° C., 3.0 g of refined product was obtained, which was a gray crystals, with purity of 97.42% and a refining yield of 60.0%. IR spectrum was the same as FIG. 4. The product was identified as ABA by IR. Its metal content was showed in Table 2.

92.25%. Its IR spectrum was showed in FIG. 1. The IR (KBr, $cm^{-1}$) absorption peak was analyzed as follows:

3422.1 (s, hydroxy), 3336.3, 3270.7 (m, N—H of amino), 3099.6, 2601.5 (m, associating state of aromatic carboxylic acid with O—H), 1697.6 (s, C=O of aromatic carboxylic acid), 1616.6 (s, C=N of oxazole), 1580.2, 1557.9 (s, C=C of benzene ring), 1490.7, 1468.7 (s, oxazole hetero cycle), 1382.1 (s, phenolic hydroxy), 1327.3 (s, C—O of aromatic carboxylic acid), 1302.7 (s, C—N of primary aromatic amine), 1278.6 (s, C—O of oxazole), 1220.9, 1114.6 (s, C—O of hydroxy), 1411.0, 1053.8 (s, C—C skeleton of benzene ring), 860.5 (s, C—H of benzene ring para-disubstituent), 709.4 (s, benzoxazole). $^1$H-NMR (DMSO): 6.94, 7.04, 8.10, 8.18. The product was determined qualitatively as 4-(5-amino-6-hydroxybenzoxazol-2-yl)benzoic acid (ABA).

TABLE 2

| Compare Exp. | Crude product | DMF/ mL | CH$_3$OH/ mL | Dissolved temp./° C. | Activated Carbon/g | CH$_3$OH precip./mL | total metal/ppm | HPLC purity/% | Ref. yield/% | Qualitative & Appearance of product |
|---|---|---|---|---|---|---|---|---|---|---|
| 1 | ABAS | 150 | 50 | 95 | 0.5 | 300 | 1172 | 98.04 | 52.0 | ABA light-gray |
| 2 | ABA | 150 | 50 | 95 | 0.5 | 300 | 296 | 98.01 | 79.0 | ABA deep-beige |
| 3 | ABA* | 170 | 50 | 98 | 0.5 | 400 | 102 | 97.42 | 60.0 | ABA Gray |

EXAMPLE 12

Preparation of ABA (4-(5-amino-6-hydroxybenzoxazol-2-yl)benzoic acid)

according to Scheme A: One-pot method by hydrolysis and then reduction 12.0 g (0.038 mol) of methyl 4-(5-nitro-6-hydroxybenzoxazol-2-yl)benzoate (MNB), 306 g of methanol, 45 g of water and 5.36 g (0.096 mol) of KOH were added into a reaction vessel. The mixture was stirred and heated to 75° C. to react under reflux condition, as the mixture turned into red floc from a yellow suspension, continued to react for 1 h. 1.2 g of ferrous chloride, 2.4 g of activated carbon and 10.2 g (0.163 mol) of 80% hydrazine hydrate were added into the reaction mixture, the resulting mixture was heated to 75° C. and reacted under reflux condition for 2 h, and the reaction mixture turned orange yellow. Waste carbon was removed by filtering while hot. 19 g of concentrated hydrochloric acid was added into the filtrate to precipitate yellow solids. After filtration, the solids were washed, and vacuum dried to obtain 9.52 g of ABA product, with purity of 96.2%, total content of metal ions (K$^+$, Fe$^{2+}$) of 3252 ppm and a yield of

EXAMPLES 13~19

Preparation of ABA (Scheme A)

ABA was prepared by the same operation of example 12, with 12 g of MNB, 10.2 g of 80% hydrazine hydrate, and different dosages of methanol, water, KOH and hydrochloric acid. The results were showed in Table 3.

TABLE 3

MNB was hydrolyzed, and then reduced with hydrazine hydrate to prepare ABA in one-pot

| Example | Methanol dosage/g | Water/g | KOH/MNB mol. ratio | Hydrolysis time/h | Reduction time/h | ABA Purity/% | ABA Totalmetal ion/ppm | ABA Yield/% |
|---|---|---|---|---|---|---|---|---|
| 13 | 170 | 30 | 2.82 | 1.5 | 3 | 96.4 | 3869 | 90.89 |
| 14 | 158 | 23 | 2.50 | 0.5 | 3 | 98.2 | 2963 | 93.14 |
| 15 | 159 | 45 | 2.56 | 1 | 1.25 | 98.0 | 3268 | 88.57 |
| 16 | 159 | 45 | 2.56 | 1 | 2 | 97.7 | 3106 | 90.99 |
| 17 | 170 | 30 | 2.82 | 2.5 | 3 | 96.4 | 3793 | 96.61 |
| 18 | 192 | 28 | 2.52 | 2 | 3.5 | 97.1 | 2840 | 84.50 |
| 19 | 192 | 23 | 2.52 | 0.75 | 4.5 | 97.0 | 3041 | 92.05 |

EXAMPLE 20

Preparation of ABA (Scheme B: Reduction and then Hydrolysis in One-Pot)

10 g (0.032 mol) of methyl 4-(5-nitro-6-hydroxybenzoxazole-2-yl)benzoate (MNB), 1.98 g of activated carbon, 1.4 g of ferric chloride, 5.9 g (0.094 mol) of 80% hydrazine hydrate and 202 g of methanol were added into a reaction vessel. The mixture was stirred and heated to refluxing temperature, after reacting for 3.5 h, the yellow reaction solution turned into brown. Then 8 g of water and 4.95 g (0.12 mol) of NaOH were added into the reduction solution, after reacting for 3 h, the materials were dissolved to obtain an orange yellow solution, then waste carbon was removed by filtering while hot, and the concentrated hydrochloric acid was added into the filtrate until the pH was 6~7 to precipitate yellow solids. After filtration, the yellow solids were washed and vacuum dried to obtain 6.35 g of ABA, with purity of 95.34%, total content of metal ions ($Na^+$, $Fe^{2+}$) of 4415 ppm and a yield of 73.84%. Its IR spectrum was the same as FIG. 1. The product was identified as ABA by IR.

EXAMPLES 21~25

Preparation of ABA (Scheme B)

Figure 5:
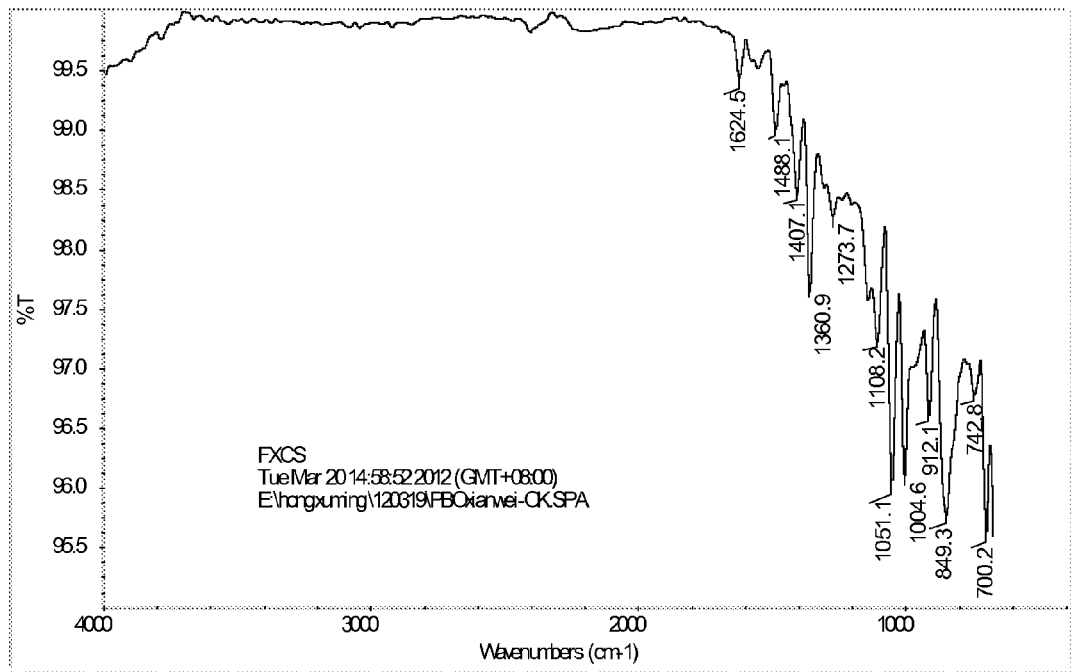
FIG. 5 is the infrared spectrum of PBO fibers.

With 10 g of MNB, different dosage of hydrazine hydrate and NaOH, and different reduction and hydrolysis time, ABA was prepared by the same operation of example 20. The conditions and results were showed in Table 4.

heated to 150° C. within 1 h, after silklike substances appeared, the mixture was heated to 160° C. and reacted for 20 min, then the polymerization reaction ended and a liquid crystal spinning solution of PBO was obtained. Fibers (about 8~15 m) were formed via directly and continuously drawing from the liquid crystal spinning solution of PBO at 120° C., repeatedly washed with boiling water until neutral, dried at 110° C. to obtain golden as-spun PBO fibers. The fibers had tensile strength of 3.9 GPa, modulus of 152 GPa, an intrinsic viscosity of 31.2 dl/g and a total yield of 96.1%. IR spectrum of the PBO fibers was showed by FIG. 5.

APPLICATION EXAMPLE 2

21.3 g of a PPA solution with a $P_2O_5$ concentration of 83.8% and 3.76 g (0.0131 mol) of ABAA prepared by example 9 were successively added into a self-made glass polymerization reactor to obtain a mixture with a. monomer concentration of 15.0 wt. %. Under the protection of nitrogen, the mixture was heated to 120° C. within 15 min and

TABLE 4

MNB was reduced with hydrazine hydrate, then hydrolyzed to prepare ABA in one-pot

| Example | Methanol dosage/g | MNB mol. ratio | $N_2H_4H_2O$/ Reduction time/h | NaOH/MNB mol. ratio | Water/g | Hydrolysis time/h | ABA Purity/% | Totalmetal ion/ppm | Yield/% |
|---|---|---|---|---|---|---|---|---|---|
| 21 | 112 | 2.47 | 3 | 3.23 | 2 | 1 | 95.14 | 3487 | 78.49 |
| 22 | 140 | 3.07 | 3 | 4.02 | 7 | 2 | 96.08 | 4672 | 93.05 |
| 23 | 149 | 2.95 | 2 | 3.09 | 7 | 1 | 95.69 | 3926 | 85.58 |
| 24 | 139 | 3.35 | 3 | 3.98 | 3 | 1 | 96.40 | 4893 | 84.53 |
| 25 | 130 | 3.20 | 3 | 4.19 | 8 | 1.5 | 95.50 | 5277 | 81.16 |

APPLICATION EXAMPLE 1

Preparation of PBO Fibers by ABAA Homo-Polycondensation 3.2 g of $P_2O_5$ and 24.0 g of PPA with a $P_2O_5$ concentration of 83% were sequentially added into a self-made glass polymerization reactor. The mixture was heated to 90° C. and stirred for 1 h until it became transparent, and then a PPA solution with a $P_2O_5$ concentration of 85% was obtained. The PPA solution was slightly cooled by introducing nitrogen to the reactor, then 4.11 g (0.0143 mol) of ABAA prepared by example 3 was added into the reactor in nitrogen atmosphere and made the concentration of ABAA be 13.1% (wt). The mixture was heated to 110° C. and stirred for 1.5 h until the monomer was dissolved. Then, the mixture was heated gradually to 125° C. within 45 min and fluoresced. The prepolymerization reaction proceeded at 125° C. for 40 min, then the reaction mixture was gradually stirred for 25 min, then the monomer was dissolved and the mixture fluoresced. After stirring at 120° C. for 1 h, the reaction system was quickly heated to 160° C., then polymerized for 45 min, when liquid crystal silklike substances appeared, the polymerization reaction ended and a liquid crystal spinning solution of PBO was obtained. Fibers (about 6~8 m) was formed via directly and continuously drawing from the PBO liquid crystal spinning solution at 120° C., repeatedly washed with boiling water until neutral, dried at 110° C. to obtain golden as-spun PBO fibers. The fibers had tensile strength of 4.05 gpa, modulus of 249 gpa and intrinsic viscosity of 38.1 dl/g.

APPLICATION EXAMPLES 3~5

With different concentration of monomer (ABAA), different concentration of $P_2O_5$ in PPA, different polymerization temperature and time, PBO fibers were prepared by the same operation of application example 1. The conditions and results were showed in Table 5.

TABLE 5

| Application examp | ABAA from Example | ABAA concn./% | $P_2O_5$ In PPA/% | Polym. temp./° C. | Polym time/h | Appearance of fibers* | Spinnability | intrinsic viscosity/ dl/g | strength/ GPa | modulus/ GPa |
|---|---|---|---|---|---|---|---|---|---|---|
| 1 | 3 | 13.1 | 85.0 | 100~160 | 2.75 | golden | Very good | 31.2 | 3.91 | 151 |
| 2 | 9 | 15.0 | 83.8 | 100~160 | 2.25 | Purple golden | Very good | 38.1 | 4.05 | 249 |
| 3 | 1(1) | 13.5 | 82.5 | 100~150 | 6.0 | golden | Very good | 23.9 | 3.68 | 163 |
| 4 | 10 | 12.0 | 83.8 | 90~140 | 4.0 | golden | Very good | 24.6 | 3.80 | 150 |
| 5 | Compare example 2 | 12.0 | 83.0 | 90~140 | 7.0 | golden | good | 18.3 | 3.18 | 155 |

*aftertreatment: The drew fibers were diluted with water, washed with boiling water and vacuum dried to prepare PBO-AS fibers of 10~150 μm diameter range.

APPLICATION COMPARE EXAMPLE 1

Preparation of PBO by ABA Homo-Polycondensation (Literature: Polymer Preprints, 1990, 31(2), 681-682)

1.163 g (4.31 mol) of ABA, 0.766 g of $P_2O_5$ and 18.188 g of 115% PPA were sequentially added into a polymerization reactor. After well stirring, oxygen was removed by introducing nitrogen under a pressure-reducing condition of 0.09 MPa at 90° C. for 3 h, then nitrogen was introduced under normal pressure for 12 h until the reaction system became transparent. The polymerization was carried out at 120° C. for 3 h, then at 150° C. for 3 h, then at 180° C. for 1 h, and finally at 190~200° C. for 2.5 h. After polymerization, the reaction mixture was put into water to precipitate solids and then filtered. The obtained filter cake was reflux washed with water for 12 h and then with acetone for 8 h, then it was vacuum dried at 175° C. for 3 h to obtain 0.94 g of PBO resin, with an intrinsic viscosity of 12.5 dl/g and a yield of 93.3%.

APPLICATION COMPARE EXAMPLE 2

Replaced ABA in Application compare example 1 with refined ABA (with purity of 97.42%, $K^+$: 39 ppm, $Na^+$: 56 ppm, Fe: 7 ppm) prepared according to the method in the Literature (Polymer preprints, 1990, 31(2), 681-682), other polymerization operation was the same as that of application compare example 1, and then PBO resin with an intrinsic viscosity of 9.2 dl/g was obtained, whose spinnability was poor.

APPLICATION COMPARE EXAMPLE 3

According to Previous Patent 1: CN 2006 10155719.8

1.8 g of ABA (the same as ABA used in Example 1(1), with purity of 98.82%, $K^+$:5489 ppm, $Na^+$:155 ppm, Fe:75 ppm), 19.48 g of PPA and 9 g of $P_2O_5$ were added into a polymerization reactor and nitrogen was introduced. The mixture was stirred and heated to 120° C., after reacting for 3 h, the reaction solution became orange, then the reaction solution was further heated to 160° C., after reacting for 3 h, the reaction solution became tenne and exhibited opalescence phenomenon; then the reaction solution was further heated to 180° C., after reacting for 2 h, the reaction solution became brownish green; finally, the reaction solution was heated to 200° C., after reacting for 3 h, the reaction solution became greenblack, and the polymerization reaction ended. The reaction mixture was cooled, put into 100 mL of water, heated to 60° C., stirred and washed twice, and dried at 105° C. for 10 h, and then 1.76 g of PBO polymer with an intrinsic viscosity of 10.31 dl/g (30° C., MSA) was obtained.

APPLICATION COMPARE EXAMPLE 4

Preparation of PBO by ABAS Homo-Polycondensation (According to Patent 2: CN 2006 10155718.3)

1.8 g of ABAS (with purity of 98.57%, $K^+$:573 ppm, $Na^+$:28390 ppm, Fe:109 ppm, no DMF), 19.48 g of PPA and 9 g of $P_2O_5$ were added into a polymerization reactor and nitrogen was introduced. The mixture was stirred and heated to 120° C. after reacting for 3 h, the reaction solution became orange; then the reaction solution was further heated to 160° C., after reacting for 3 h, the reaction solution became tenne and exhibited opalescence phenomenon; then the reaction solution was further heated to 180° C., after reacting for 2 h, the reaction solution became brownish green; finally, the reaction solution was further heated to 200° C., after reacting for 3 h, the reaction solution became greenblack, and the polymerization reaction ended. The reaction mixture was cooled, put into 100 mL of water, heated to 60° C., stirred and washed twice, dried at 105° C. for 10 h, and then 1.76 g of PBO polymer with an intrinsic viscosity of 13.1 dl/g (30° C., MSA) was obtained.

The conditions and results of application compare examples were showed in Table 6.

TABLE 6

| Application compare example | Monomer Abbreviations | Monomer concn./% | $P_2O_5$ in PPA/% | Polym. temp./° C. | Polym time/h | Appearance of PBO | Spinnability | [η]/ dl/g |
|---|---|---|---|---|---|---|---|---|
| 1 | ABA | 5.8 | 85.0 | 120~200 | 9.5 | copper | — | 12.5 |
| 2 | ABA* | 5.8 | 85.0 | 120~200 | 9.5 | green-brown | Poor | 9.2 |
| 3 | ABA | 6.0 | 86.3 | 120~200 | 11.0 | Brown | Good | 10.3 |
| 4 | ABAS | 6.0 | 86.3 | 120~200 | 11.0 | Brown | Good | 13.1 |

APPLICATION EXAMPLE 6

ABAA applied in the preparation of modified PBO fibers which is modified with poly-2,6-benzoxazole)(PBO°)

(1) Synthesis of R-PBO Fibers (the Molecular Link Ratio of PBO°: PBO=1.7:1.0)

Figure 6A:
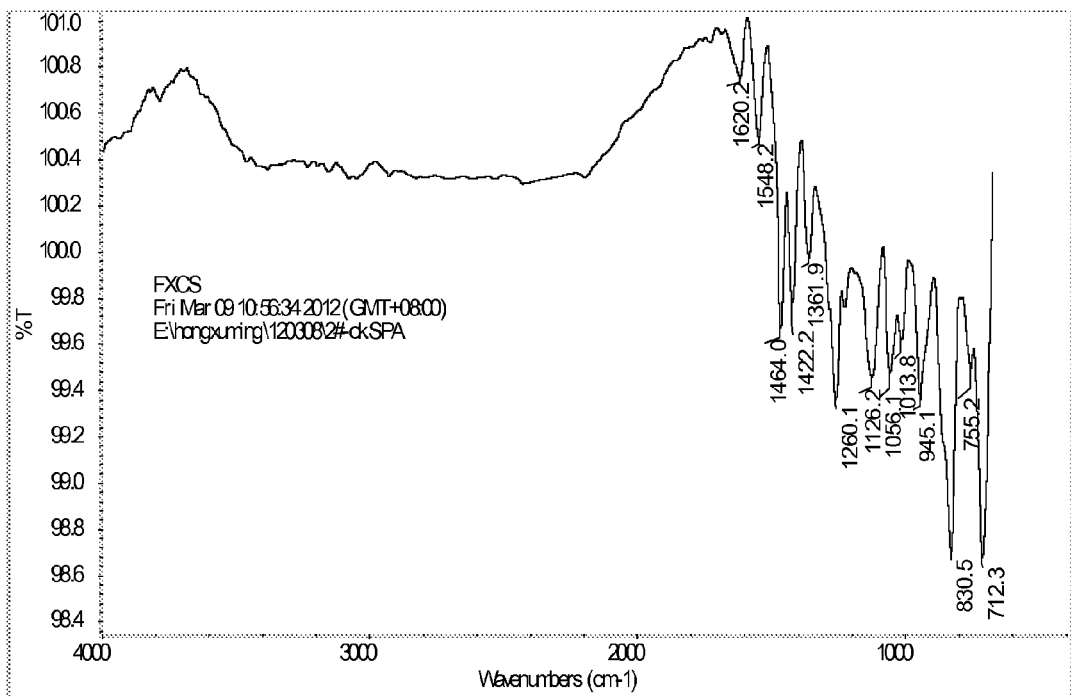
FIGS. 6a) and 6b) are respectively the infrared spectrum of PBO fibers modified by R (poly-2,6-benzoxale, PBO°).
Figure 6B:
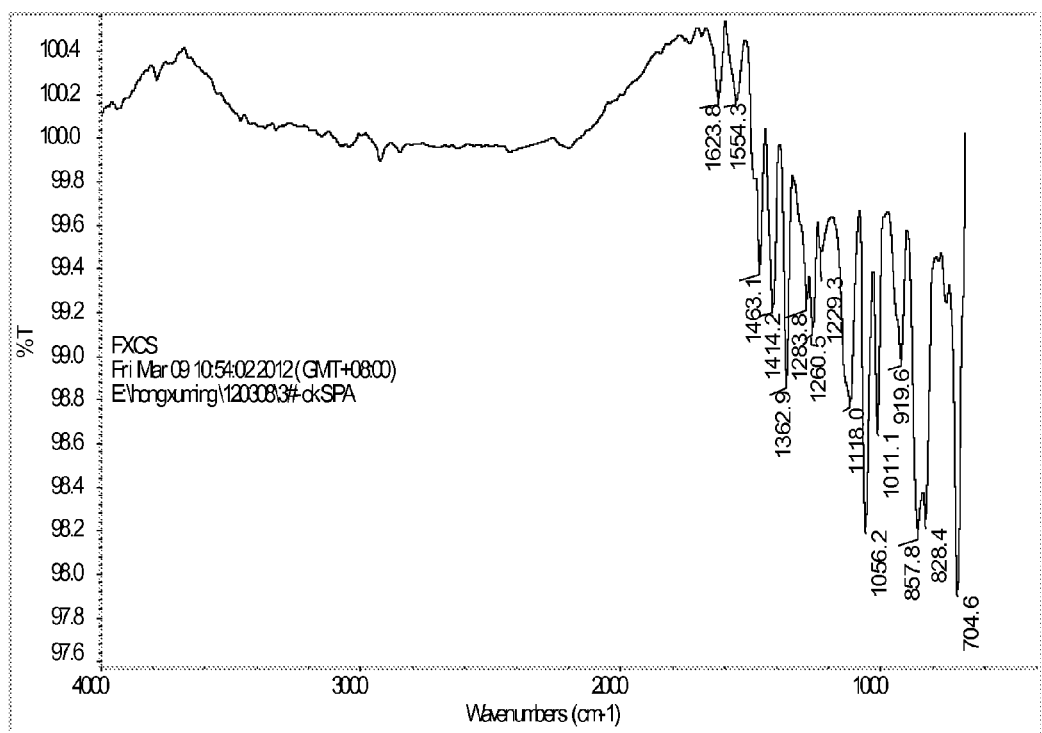

19.66 g of PPA was added into a polymerization reactor, and then heated to 80° C. 4.75 g of $P_2O_5$ was added, and the mixture was stirred until $P_2O_5$ was dissolved. 1.5 g of 4-amino-3-hydroxybenzoic acid (HABA) and 1.5 g of ABAA prepared by example 10 were added into the reactor. Raised the temperature to 100° C. and stirred for 3 h, then raised to 130° C. and stirred for 1 h, and then the reaction system became viscous and difficult to stir. When the temperature was raised to 150° C., the reaction system became dilute and had good fluidity, continued to react for 1 h, and the polymerization reaction ended. After the wire drawing, the resulting fibers were repeatedly washed with boiling water until neutral and vacuum dried at 100° C. to obtain as-spun R-PBO fibre mainly comprising poly-2,6-benzoxazole) (PBO°), which had an intrinsic viscosity of 14.6 dl/g, a decomposition temperature of 641.6° C. and tensile strength of 2.86 GPa. Its IR spectrum was showed in FIG. 6-a.

(2) Synthesis of R-PBO (Molecular Link Ratio of PBO° to PBO was 0.44:1.0) Fibers 23.68 g of PPA was added into a polymerization reactor, then heated to 80° C., then 5.95 g of $P_2O_5$ was added, the mixture was stirred until $P_2O_5$ was dissolved, then 0.89 g of 4-amino-3-hydroxybenzoic acid (HABA) and 3.55 g ABAA prepared by example 10 were added into the reactor, the mixture was stirred for 0.5 h, then heated to 120° C., after reacting for 0.5 h, the reaction mixture was further heated to 126° C., bubble and fluorescence at the bottom appeared; then the mixture was further heated to 130° C., after stirring for 1 h, liquid crystallines appeared, after reacting for another 1 h, the mixture was then heated to 140° C., after reacting for 0.5 h, bubble disappeared, then the mixture was further heated to 155° C., after reacting for 0.5 h, further heated to 170° C., and then the polymerization reaction ended. After the wire drawing, the resulting fibers were repeatedly washed with boiling water until neutral and vacuum dried at 100° C. to obtain as-spun R-PBO fibre mainly comprising PBO, which had an intrinsic viscosity of 16.1 dl/g, a decomposition temperature of 669.8° C. and tensile strength of 3.23 GPa. Its IR spectrum was showed in FIG. 6-b.

What is claimed:

1. Ammonium 4-(5-amino-6-hydroxybenzoxazole-2-yl) benzoate, which is represented by the formula (I):

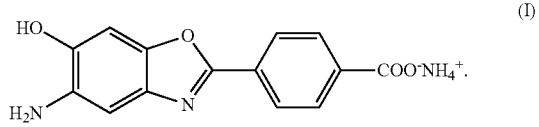

2. A method of preparing ammonium 4-(5-amino-6-hydroxybenzoxazol-2-yl) benzoate as claimed in claim 1, includes the following step:
1) using 4-(5-amino-6-hydroxybenzoxazol-2-yl)benzoic acid of formula (II) or 4-(5-amino-6-hydroxybenzoxazol-2-yl) benzoic acid carboxy-amino inner salt of formula (III) as a raw material, reacting the raw material with ammonia in water, after the reaction is completed, removing excess ammonia from the reaction solution by heating and keeping water content in the reaction solution constant during the process of removing ammonia, then cooling the reaction solution, subjecting it to filtration, washing and drying the solids to obtain ammonium 4-(5-amino-6-hydroxybenzoxazol-2-yl)benzoate (ABAA);

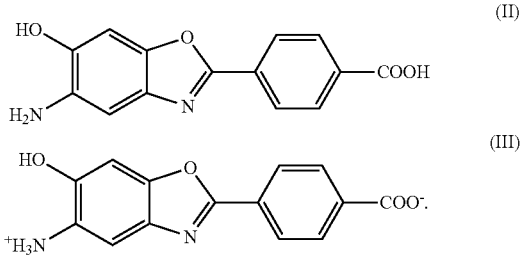

3. The method as claimed in claim 2, wherein the method also include a refining step 2) as follows:
2) dissolving ammonium 4-(5-amino-6-hydroxybenzoxazol-2-yl)benzoate with ammonia water to obtain an ABAA solution, heating the solution to remove excess ammonia, keeping the content of water in the system constant during the process of ammonia removal, then cooling the reaction solution, subjecting it to filtration, washing and drying the solids to obtain refined ammonium 4-(5-amino-6-hydroxybenzoxazol-2-yl)benzoate.

4. The method as claimed in claim 2, wherein, in step 1), the molar ratio of ammonia to 4-(5-amino-6-hydroxybenzoxazol-2-yl)benzoic acid or 4-(5-amino-6-hydroxybenzoxazol-2-yl) benzoic acid carboxy-amino inner salt is between 8:1 and 30:1, the water is 16~70 times the weight of 4-(5-amino-6-hydroxybenzoxazol-2-yl)benzoic acid or 4-(5-amino-6-hydroxybenzoxazol-2-yl)benzoic acid carboxy-amino inner salt.

5. The method as claimed in claim 3, wherein, in step 2), the molar ratio of ammonia to ammonium 4-(5-amino-6-hydroxybenzoxazol-2-yl)benzoate is between 8:1 and 30:1, the water is 16~70 times the weight of ammonium 4-(5-amino-6-hydroxybenzoxazol-2-yl)benzoate.

6. The method as claimed in any one of claims 2 to 5, wherein said step 1) also includes a step of impurity removal as follows: adding activated carbon into the reaction solution to absorb the impurities, then subjecting the reaction system to filtration to remove waste carbon, and then directly heating the filtrate to remove excess ammonia.

7. The method as claimed in claim 3 or 5, wherein said step 2) also includes a step of impurity removal as follows: adding activated carbon into the ABAA solution to absorb impurities, then subjecting the mixture to filtration to remove waste carbon, and directly heating the filtrate to remove excess ammonia.

8. The method as claimed in any one of claims 2 to 5, wherein said step 1) also includes an antioxidation step as follows: adding ammonium sulfite to the reaction solution as an antioxidant, and then directly heating the mixture to remove excess ammonia.

9. The method as claimed in claim 6, wherein said step 1) also includes an antioxidation step as follows: adding ammonium sulfite to the filtrate obtained in the step of impurity removal as an antioxidant, and then directly heating the mixture to remove excess ammonia.

10. The method as claimed in claim 3 or 5, wherein said refining step 2) also includes an antioxidation step as follows: adding ammonium sulfite to the ABAA solution as an antioxidant, and then directly heating the mixture to remove excess ammonia.

11. The method as claimed in claim 7, wherein said refining step 2) also includes an antioxidation step as follows: adding ammonium sulfite to the filtrate obtained in the step of impurity removal as an antioxidant, and then directly heating the mixture to remove excess ammonia.

12. The method as claimed in claim 2, wherein in step 1), the reaction of the raw material with ammonia is carried out at a temperature between 40° C. and 80° C. with stirring until dissolved; and removing excess ammonia by heating is carried out at a temperature not higher than 80° C. until the pH of the reaction system reaches 7.0 to 7.5.

13. The method as claimed in claim 3, wherein in step 2), dissolving ammonium 4-(5-amino-6-hydroxybenzoxazol-2-yl)benzoate with ammonia water is carried out at a temperature ranging from 40° C. to 80° C. with stirring; and removing excess ammonia by heating is carried out at a temperature not higher than 80° C. until the pH of the reaction system reaches 7.0 to 7.5.

14. The method as claimed in claim 2, wherein the raw material 4-(5-amino-6-hydroxybenzoxazol-2-yl)benzoic acid of formula (II) is prepared by subjecting methyl 4-(5- nitro-6-hydroxybenzoxazol-2-yl)benzoate of formula (IV) to hydrolysis of ester group and then reduction of nitro group (Scheme A), or by subjecting methyl 4-(5-nitro-6-hydroxybenzoxazol-2-yl)benzoate of formula (IV) to reduction of nitro group and then hydrolysis of ester group (Scheme B); in which, the reduction of nitro group uses hydrazine hydrate as a reductant and $Fe^{2+}/C$ or $Fe^{3+}/C$ as a catalyst, the catalyst $Fe^{2+}/C$ is composed of activated carbon and a water-soluble ferrous salt, and the catalyst $Fe^{3+}/C$ is composed of activated carbon and a water-soluble ferric salt;

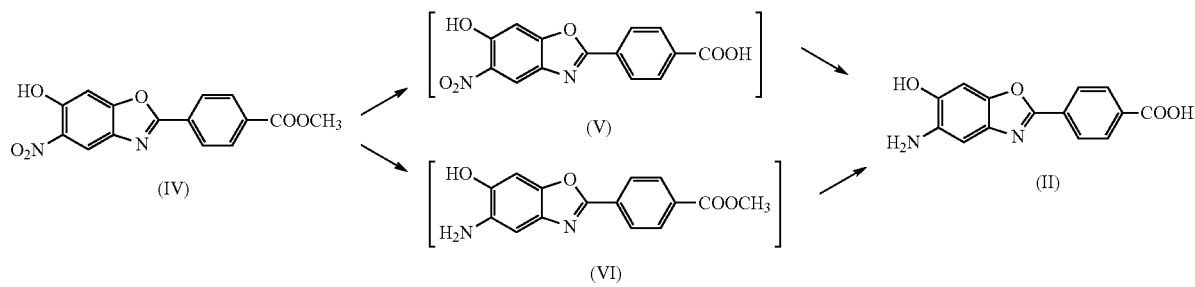

said Scheme A is carried out as follows:
add methyl 4-(5-nitro-6-hydroxybenzoxazole-2-yl)benzoate of formula (IV), an alcohol-water solvent and KOH, carry out hydrolysis of ester group under alkaline condition to obtain 4-(5-nitro-6-hydroxybenzoxazol-2-yl)benzoic acid of formula (V); then without any separation add $Fe^{2+}/C$ or $Fe^{3+}/C$ and hydrazine hydrate to the reaction system to carry out reduction of nitro group, subject the reaction solution to aftertreatment to obtain 4-(5-amino-6-hydroxybenzoxazol-2-yl)benzoic acid of formula (II);
and said Scheme B is carried out as follows:
add methyl 4-(5-nitro-6-hydroxybenzoxazole-2-yl)benzoate of formula (IV), an alcohol solvent, $Fe^{2+}/C$ or $Fe^{3+}/C$ and hydrazine hydrate, carry out reduction of nitro group to obtain methyl 4-(5-amino-6- hydroxybenzoxazole-2-yl)benzoate of formula (VI), then without any separation add NaOH and water to carry out hydrolysis of ester group, subject the reaction solution to aftertreatment to obtain 4-(5-amino-6-hydroxybenzoxazol-2-yl)benzoic acid of formula (II).

15. The method as claimed in claim 14, wherein Scheme A is specifically carried out as follows:
add methyl 4-(5-nitro-6-hydroxybenzoxazole-2-yl)benzoate of formula (IV) (MNB), alcohol, water and KOH to a reactor, heat the mixture to reflux temperature with stirring and react for 0.5 h to 2.5 h; add the catalyst $Fe^{2+}/C$ or $Fe^{3+}/C$ and hydrazine hydrate to the reaction mixture, then add some alcohol, heat the obtained mixture to reflux temperature and react for 1.25 h to 4.5 h, after the reaction is complete, subject the resulting reaction mixture to filtration while hot to remove waste carbon, the filtrate is added with hydrochloric acid to precipitate solids and filtered, the solids are washed with water and vacuum dried to obtain 4-(5-amino-6-hydroxybenzoxazol-2-yl)benzoic acid; in which, the weight ratio of water to MNB is between 1.9:1 and 3.8:1, the weight ratio of alcohol to MNB is between 13:1 and 26:1, the molar ratio of KOH to MNB is between 2.50:1 and 2.82:1, the molar ratio of hydrazine hydrate to MNB is between 4:1 and 4.5:1, the weight ratio of the water-soluble ferrous or ferric salt to MNB is between 0.08:1 and 0.12:1, and the weight ratio of activated carbon to MNB is between 0.17:1 and 0.21:1.

16. The method as claimed in claim 14, wherein Scheme B is specifically carried out as follows:
add methyl 4-(5-nitro-6-hydroxybenzoxazole-2-yl)benzoate of formula (IV) (MNB), the catalyst $Fe^{2+}/C$ or $Fe^{3+}/C$, hydrazine hydrate and an alcohol to a reactor, heat the mixture to reflux temperature with stirring and react for 2 h to 4 h; add NaOH and water to the reaction mixture, continue to react at reflux temperature for 1 h to 3 h, after the reaction is complete, the resulting reaction mixture is filtered while hot to remove waste carbon, the filtrate is added with hydrochloric acid to precipitate yellow solids and filtered, the solids are washed with water and vacuum dried to obtain 4-(5-amino-6-hydroxybenzoxazol-2-yl)benzoic acid; in which, the alcohol is 11.2~20.5 times the weight of MNB, the molar ratio of hydrazine hydrate to MNB is between 2.47:1 and 3.35:1, the weight ratio of the water-soluble ferric or ferrous salt to MNB is between 0.12:1 and 0.15:1, the weight ratio of activated carbon to MNB is between 0.18:1 and 0.21:1, the molar ratio of NaOH to MNB is between 3.09:1 to 4.19:1, and the water is 0.2~0.8 times the weight of MNB.

17. A method of preparing PBO of formula (VII) or modified PBO of formula (VIII), the method comprising:
obtaining ammonium 4-(5-amino-6-hydroxybenzoxazole-2-yl)benzoate (ABAA) as claimed in claim 1; and
using ABAA as a monomer in preparing PBO of formula (IV) by homo-polycondensation or modified PBO of formula (VIII) by co-polycondensation.

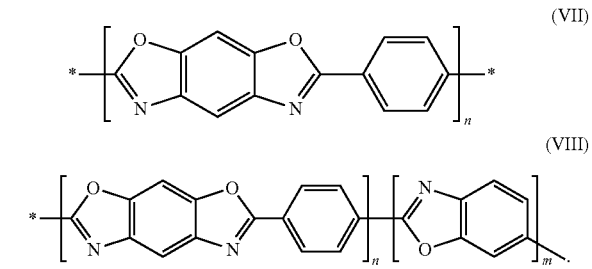

18. The method of claim 17, wherein the method comprises: using polyphosphoric acid as a solvent and phosphorus pentoxide as a dehydrating agent, subjecting ammonium 4-(5-amino-6-hydroxybenzoxazole-2-yl)benzoate to homo-polycondensation to obtain a liquid crystalline solution of PBO or subjecting ammonium 4-(5-amino-6-hydroxybenzoxazole-2-yl)benzoate and 4-amino-3-hydroxybenzoic acid to co-polycondensation to obtain a liquid crystalline solution of modified PBO, and then preparing PBO of formula (IV) or modified PBO of formula (V) fibers by dry-jet wet spinning of the liquid crystalline solution.

19. The method of claim 18, wherein preparing PBO fibers includes the following steps:
1) adding ammonium 4-(5-amino-6-hydroxybenzoxazole-2-yl)benzoate (ABAA) into polyphosphoric acid with a concentration of $P_2O_5$ more than 84 wt. % until the mass concentration of ABAA is between 12% and 15%, heating the mixture gradually to a temperature between 100° C. and 160° C. and reacting for 2 h to 5 h to obtain a liquid crystal spinning solution of PBO; and
2) directly and continuously subjecting the liquid crystal spinning solution of PBO to wire drawing and then aftertreatment to obtain PBO fibers of formula (IV).

20. The method of claim 18, wherein preparing modified PBO fibers includes the following steps:
a) adding monomers composed of 4-(5-amino-6-hydroxybenzoxazole-2-yl)benzoate (ABAA) and 4-amino-3-hydroxybenzoic acid with a mass ratio of ABAA to 4-amino-3-hydroxybenzoic acid between 60% to 40% and 80% to 20% into polyphosphoric acid with a concentration of $P_2O_5$ more than 84 wt. % until the total mass concentration of the monomers is between 12% and 15%, heating the mixture gradually to a temperature between 80° C. and 170° C. and reacting for 2 h to 5 h to obtain a liquid crystal spinning solution of modified PBO; and
b) directly and continuously subjecting the liquid crystal spinning solution of modified PBO to wire drawing and then aftertreatment to obtain modified PBO fibers of formula (V).

* * * * *